United States Patent
Kumakhov

(10) Patent No.: US 7,231,015 B2
(45) Date of Patent: Jun. 12, 2007

(54) DEVICE FOR RADIATION THERAPY

(76) Inventor: Muradin Abubekirovich Kumakhov, ul. Narodnogo Opolcheniya, d. 38, kv. 55, Moscow (RU) 123298

( * ) Notice: Subject to any disclaimer, the term of this patent is extended or adjusted under 35 U.S.C. 154(b) by 0 days.

(21) Appl. No.: 10/276,060

(22) PCT Filed: Sep. 19, 2001

(86) PCT No.: PCT/RU01/00384

§ 371 (c)(1),
(2), (4) Date: Nov. 13, 2002

(87) PCT Pub. No.: WO03/024527

PCT Pub. Date: Mar. 27, 2003

(65) Prior Publication Data

US 2004/0013230 A1    Jan. 22, 2004

(51) Int. Cl.
*A61N 5/10* (2006.01)
(52) U.S. Cl. .......................................... 378/65; 378/147
(58) Field of Classification Search ............ 378/64–65, 378/147, 149, 84; 600/427; 604/20–21
See application file for complete search history.

(56) References Cited

U.S. PATENT DOCUMENTS 5,153,900 A    10/1992  Nomikos ..................... 378/65
5,744,813 A *  4/1998   Kumakhov ............... 250/505.1

(Continued)

FOREIGN PATENT DOCUMENTS

RU    2120787    10/1998
WO    01/29845    5/2000
WO    02/02188    7/2000

OTHER PUBLICATIONS

Stavitskij, "Aspects of Clinical Dosimetry," Moscow, "MNPI," 2000, pp. 1-9 and 386-388 (in Russian); and extract of contents (in English).
E.S. Kiseleva, "Radiation Therapy of Malignant Tumors. Guide for Physicians," Moscow, "Meditsina" Publishing Houe, 1996, pp. 1-79 and 460 (in Russian); and extract of contents (in English).

(Continued)

*Primary Examiner*—Hoon Song
(74) *Attorney, Agent, or Firm*—McDermott Will & Emery LLP

(57) ABSTRACT

Device, related to the means for radiation therapy of malignant and benign neoplasms and certain other diseases, comprise hollow probe 5, source 1 of neutral particle radiation in the form of X-ray or gamma quanta or neutrons, and means of shaping the particle beam of said radiation oriented by the longitudinal axis of the probe. Means of shaping the particle beam is executed in the form of collimator or lens 18 comprising aggregate of curved channels for radiation transmission with a total internal reflection. Said means may be located inside of the probe 5.

On using the device, probe 5 is introduced into the body of patient 11, with its distal end 7 approaching pathological locus 13 or inserted directly into it.

For exposure of pathological locus, use is made of radiation of the neutral particles source directly or secondary radiation excited in the target placed in the distal end of the probe or radiation dissipated with this target.

Design of the device requires no evacuation of the probe and use of high voltage in the latter, is easily transformed by the probe replacement, in particular, to change its size, to change energy and directional pattern of radiation affecting the pathological locus. Making of the probe removable simplifies its sterilization.

11 Claims, 7 Drawing Sheets

U.S. PATENT DOCUMENTS

| | | | |
|---|---|---|---|
| 6,181,770 B1 * | 1/2001 | Ciravolo et al. | 378/117 |
| 6,285,735 B1 * | 9/2001 | Sliski et al. | 378/65 |
| 6,389,100 B1 * | 5/2002 | Verman et al. | 378/84 |
| 6,477,237 B1 * | 11/2002 | Taniguchi et al. | 378/145 |
| 6,580,940 B2 * | 6/2003 | Gutman | 600/427 |

OTHER PUBLICATIONS

Larsson, Crawford, and Weinreich, Advances in Neutron Capture Therapy vol. II, Chemistry and Biology; Elsevier 1997, pp. iv-xv.

Kumakhov, "Optics of Beams," Institute for Roentgen Optical Systems, Moscow 1993, pp. 1-17.

* cited by examiner

DEVICE FOR RADIATION THERAPY

FIELD OF THE INVENTION

The present invention relates to means for radiation therapy of malignant and benign neoplasms and certain other diseases.

BACKGROUND OF THE INVENTION

At present, treatment with ionizing radiation is widely used not only in the therapy of malignant neoplasms, but benign tumors and a series of inflammatory and other diseases of nonneoplastic nature as well (Aspects of Clinical Dosimetry, Ed. R. V. Stavitskij, Moscow, "MNPI", 2000 [1] (in Russian)).

Devices are known for radiation therapy which comprise X-ray source, oriented for the purpose of directing radiation created with it to the pathological locus area. In order to minimize irradiation of healthy tissues surrounding pathological locus, such devices may comprise several X-ray sources. The irradiation created with them is directed to the pathological locus area from different directions (Radiation Therapy of Malignant Tumors. Guide for Physicians. Ed. Prof. E. S.Kiseleva, Moscow, "Meditsina" Publishing House, 1996 [2] (in Russian)).

Device is also known for radiation therapy comprising several X-ray sources whose radiation, being aimed to the area of pathological locus from different directions, is focused with X-ray lenses (international application PCT/RU 00/00273, WO 01/29845A16 26 Apr. 2001 [3]). Due to the said focusing, radiation from each of the lenses on passing through the healthy tissues has in them lower concentration than in the pathological locus.

More radical way to decrease irradiation of healthy tissues surrounding the pathological locus comprise its irradiation not from outside, but from the inside.

Such a way is realized, in particular, by implantation of a capsule with radioactive material directly into the pathological locus [2]. This method has drawbacks of the necessity of surgical intervention and associated with it difficulty in the control of irradiation duration.

The most close to the device proposed is a known device disclosed in U.S. Pat. No. 5,153,900 [4] (Russian analogue patent No. 2,155,413) and in number of other patents belonging to Photoelectron Corporation. This known device comprise a probe device for introduction directly into the pathological locus or for approaching it. Probe device in said device is a part of X-ray tube. Its anode is situated at the distal end of probe device. Proximal end of probe device adjoins the outlet of means for electronic beam formation, which is directed along the longitudinal axis of the probe device towards anode.

Within the probe of this device vacuum should be maintained (as within any X-ray tube). This fact in combination with the necessity of high voltage supply to the anode situated at distal end of a thin lengthy probe and the necessity to control position of electronic beam make for design complexity of the device. At that, radiation energy is determined substantially by anode material. Impossibility of anode replacement in the evacuated probe results in necessity of having separate device for each radiation energy desired. The same is true for changing spatial radiation pattern by matching the radiotransparency ratio of different portions of the distal probe end. Operation of the device utilizing electronic beam is influenced with external magnetic fields, thus necessitating to make arrangements on corresponding shielding. Realization of the probe as a part of X-ray tube complicates substantially its sterilization. Overcoming of this drawback by providing the probe with removable sheath increases its diameter and is associated with a rise in traumatism on utilization of the device. Therefore, primary field of utilization of said device is treatment of tumors of hollow organs requiring no puncturing and situated in immediate communication with outer environment, such as urinary bladder, rectum, etc. Besides, said device, comprising probe as a constituent part of X-ray tube, is applicable for treatment with X-ray radiation only.

DISCLOSURE OF THE INVENTION

It is an object of the present invention to provide for technical result consisting in:
  possibility of application for therapy utilizing not only X-ray, but other kinds of radiation as a flux of neutral particles as well;
  design simplification and costs reduction due to avoidance of utilization of vacuum and high voltage, and elimination of control means of electronic beam and magnetic shielding;
  easy transformation by the way of probe replacement, in particular, for changes of its size, and changes in energy and directional radiation pattern acting on the pathological locus;
  simplicity of the probe sterilization, and possibility of utilization of interchangeable or disposable probes;
  possibility of the probe disconnection from the rest of device, leaving it in patient's body, and utilization of the device at this time with other probe.

In order to achieve mentioned kinds of technical result the proposed device for radiation therapy, similar to the known one mentioned above, comprises probe device for introduction into patient's body and approaching of its distal end to pathological locus or immediate introduction into it, irradiation source, and means of formation of particle beam of said radiation, oriented along the longitudinal axis of said probe.

Distinction of the proposed device from the known one lies in the fact of said radiation source being the source of neutral particles in the form of X-ray ones or gamma quanta or neutrons. At that, means of formation of particle beam of said radiation, oriented along the longitudinal axis of the probe, is executed as collimator or lens, comprising aggregate of curved channels for radiation transmittance with a total internal reflection.

With such design of the proposed device, as distinct from the known one, pathological locus is acted upon immediately with radiation of the neutral particles source used, coming through thin probe to the pathological locus or into it. Said radiation, notwithstanding the fact of being created with a source situated outside of body of the ill person, doesn't affect healthy tissues on the way to the pathological locus. This is achieved due to its propagation inside of the probe.

Due to the absence of vacuum and high electric voltage in the probe it may be executed as a removable one, thus making easy its sterilization. The device may be provided with a set of probes having different size.

The probe, except for its distal end or its separate portions, may be executed non-transparent for the particles emitted with radiation source and intended for action on the pathological locus.

Means of the particle beam formation oriented along the longitudinal axis of the probe may be situated both outside of the probe—between it and the source of high energy neutral particles—and partially or wholly inside of the probe.

In the case of the means of particle beam formation oriented along the longitudinal axis of the probe situated wholly inside of the probe and being a collimator, the latter may have single channel.

In the case of the means of particle beam formation oriented along the longitudinal axis of the probe being executed in the form of a lens comprising aggregate of curved channels for radiation transmittance with a total internal reflection, such a lens may be, in particular, a focusing lens with a focus situated outside of the probe on continuation of its longitudinal axis. In this case, focus is located within patient's body near to or inside of the pathological locus.

Said lens may be also a lens for formation of quasi-parallel beam passing through the probe and going out from its distal end.

In the case of radiation source being an X-ray source, the latter may be executed with a sectioned anode for on-line change in particle energy.

A secondary target may be located at the distal end of the probe. In this case, source radiation dissipated by secondary target or excited radiation of the secondary target material is used for radiation exposure.

In the case of the means of particle beam formation oriented along the longitudinal axis of the probe being made in the form of lens comprising aggregate of curved channels for radiation transmittance with a total internal reflection, such a lens may be, in particular, a focusing lens with a focus located on the secondary target.

In order to change characteristics of radiation dissipated and excited in the secondary target material, distal end of the probe may be made split with a possibility of replacement of the secondary target mounted in it. At that, secondary target mounted in the distal end of the probe is one of the several in the device set supplied, for example, made of different metals.

For the on-line change of desired directional radiation pattern emanating from the distal end of the probe and acting on the pathological locus, distal end of the probe may be made removable. In this case, probe has one of the several distal ends from the device set, executed with different transparency ratios of portions of the distal end surface of the probe for radiation dissipated and excited in the secondary target material.

In order to ensure coagulation of wound channel arising in the course of puncture with a probe after completion of treatment procedure, the latter may be made electrically conductive and having on the outside, except for the most remote portion of the distal end, insulating coating. In this case, the probe should have possibility of being connected to electrocoagulator.

BRIEF DESCRIPTION OF DRAWINGS

The inventions proposed are illustrated with drawings, in which are depicted.

THE EMBODIMENTS OF THE INVENTION

Figure 1:
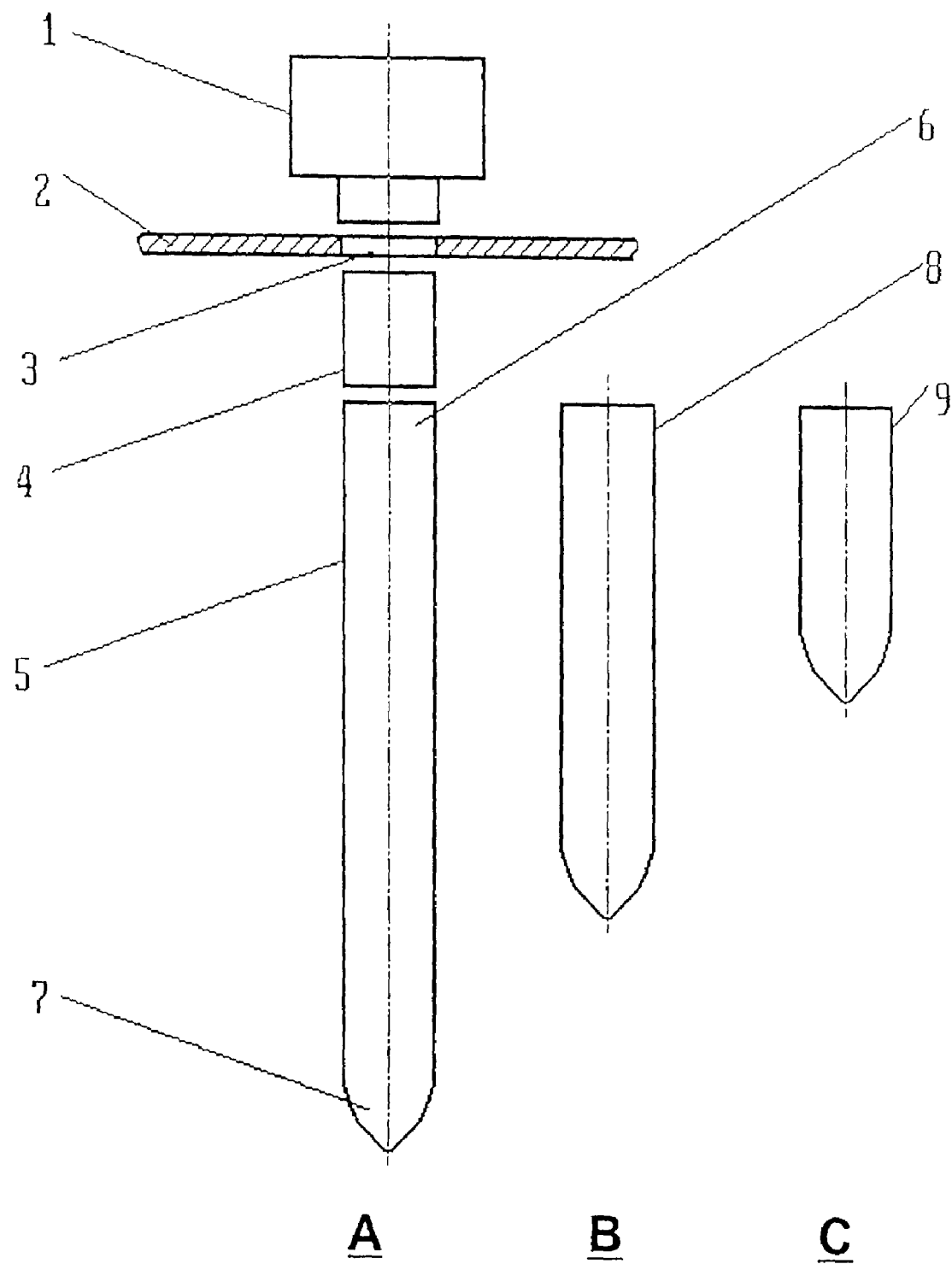
FIG. 1 - schematic representation of the device as a whole together with several probes coming in the set.

The device proposed comprises (FIG. 1, A) a source of neutral particles (X-ray or gamma quanta or neutrons), protective shield 2 with a diaphragm 3 situated in front of the outlet aperture of source 1, means 4 of formation of particle beam oriented along longitudinal axis of the probe 5. The latter has tapered distal end 7. Proximal end 6 of the probe 5 may be executed in such a way as to ensure possibility of the probe removal (for example, for sterilization and replacement with another one). The set of the device may include several probes, for example, of different length (FIGS. 1, B and C).

The probe may be similar in form and dimensions to a puncture needle for biopsy.

In the course of device usage the probe is introduced, depending on the localization of pathological locus, into one of the natural passages of patient's body or perform puncturing similar to biopsy procedure.

Figure 2:
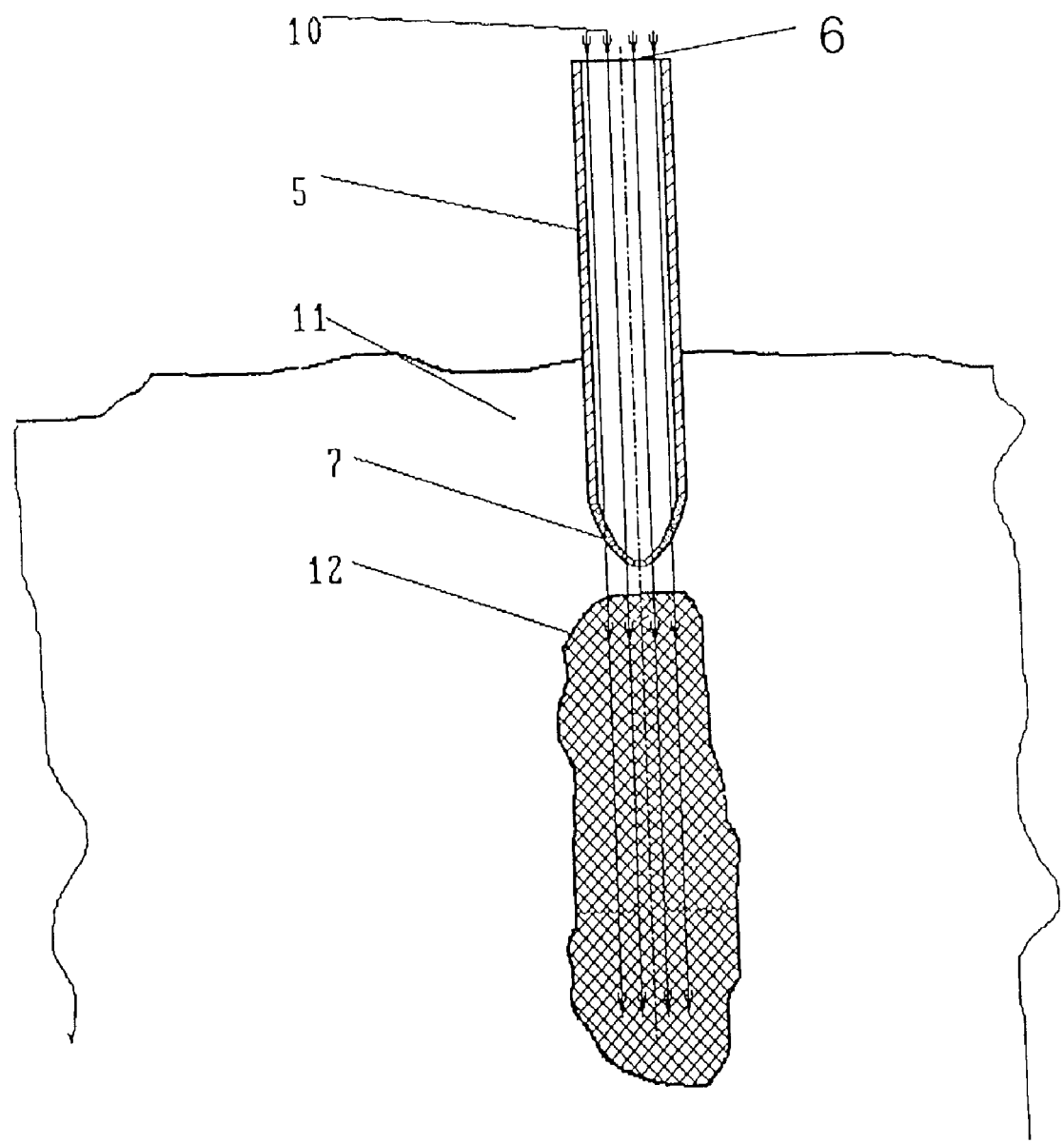
FIG. 2 - utilization of the device for irradiation of extended tumor.

FIG. 2 shows position of the probe 5 in the body of patient 11. Quasi-parallel beam 10 of radiation comes to the proximal end 6 of the probe. This beam is transmitted through the inner channel of the probe 5 and goes out through radiolucent distal end 7. The latter in the case shown in FIG. 2 is situated in the immediate proximity of extended tumor 12. The direction of the probe introduction is selected so that the radiation outgoing from the distal end 7 would enter the tumor 12 and propagate in the direction of a larger dimension. The radiation penetrating into the tumor affects directly tissues in median part of the tumor situated in its way. Tumor tissues surrounding the median ones are affected with the secondary radiation excited in the median tissues. Since radiation emerging from the distal end of the probe has practically no effect on the healthy tissues, the intensity of primary radiation of the source may be selected in such a way as to ensure that the intensity of secondary radiation of the median tissues reaching tumor periphery is on the level with that minimally sufficient for damaging peripheral tissues. In this case, secondary radiation reaching beyond tumor limits will not damage healthy tissues, which surround it.

Figure 3:
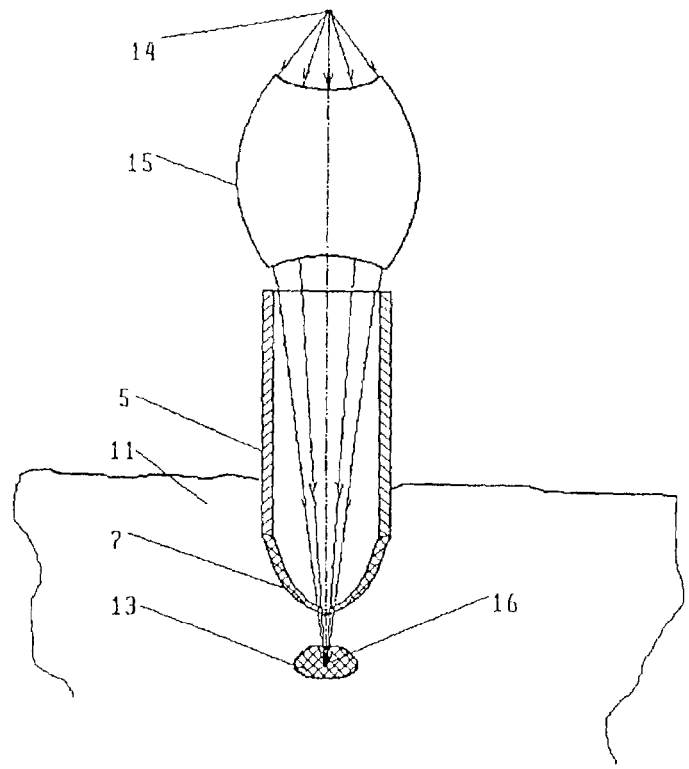
FIG. 3 - utilization of the device with lens positioned outside of the probe for irradiation of a small tumor.

To affect neoplasms having small size, it is expedient to use a focused beam outgoing from the distal end 7 of the probe 5. FIG. 3 shows embodiment of the device in which divergent radiation from X-ray source having small aperture 14 is focused with a X-ray lens 15 and transmitted through a probe 5 introduced into the body of patient to the center 16 of tumor 13. Similar to the above considered case, peripheral tissues of the tumor 13 are irradiated with excited secondary emission.

When using a source of neutrons as radiation source, use of the device proposed may be combined with a method of boron capturing therapy which ensures boron concentration in the tumor 5 (Advances in Neutron Capture Therapy. Editors: B. Larsson, J. Crawford, R. Weinrech. Elsevier, 1997 [5]).

Up-to-date technology of X-ray manufacturing allows to obtain single piece lenses of a small size (see, for example, M. A.Kumakhov. A history of the X-Ray and neutron capillary optics. Optic of beams, p.p. 3-17, Moscow, 1993 [6]), acceptable for placement partially or totally inside of the probe. Corresponding embodiments of the device are shown in FIG. 4 and FIG. 5.

Figure 4:
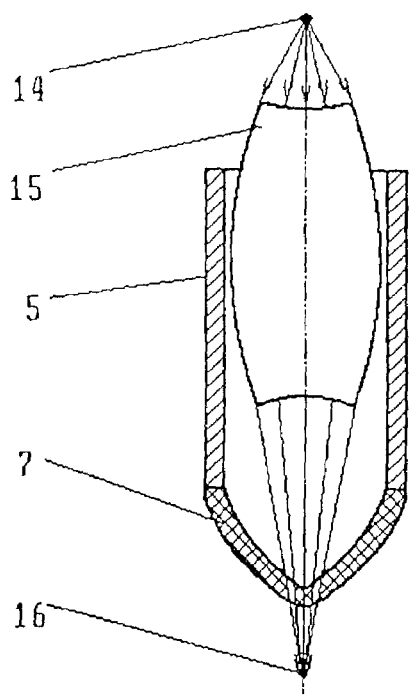
FIG. 4 - lens positioning partially inside of the probe.

In FIG. 4, focusing lens 15 is situated inside of the probe 5, with divergent radiation from the source having small aperture 14 coming in at the input. Focusing is accomplished in the point 16 situated outside of the radiolucent distal end 7 of the probe 5 on the continuation of its longitudinal axis.

Figure 5:
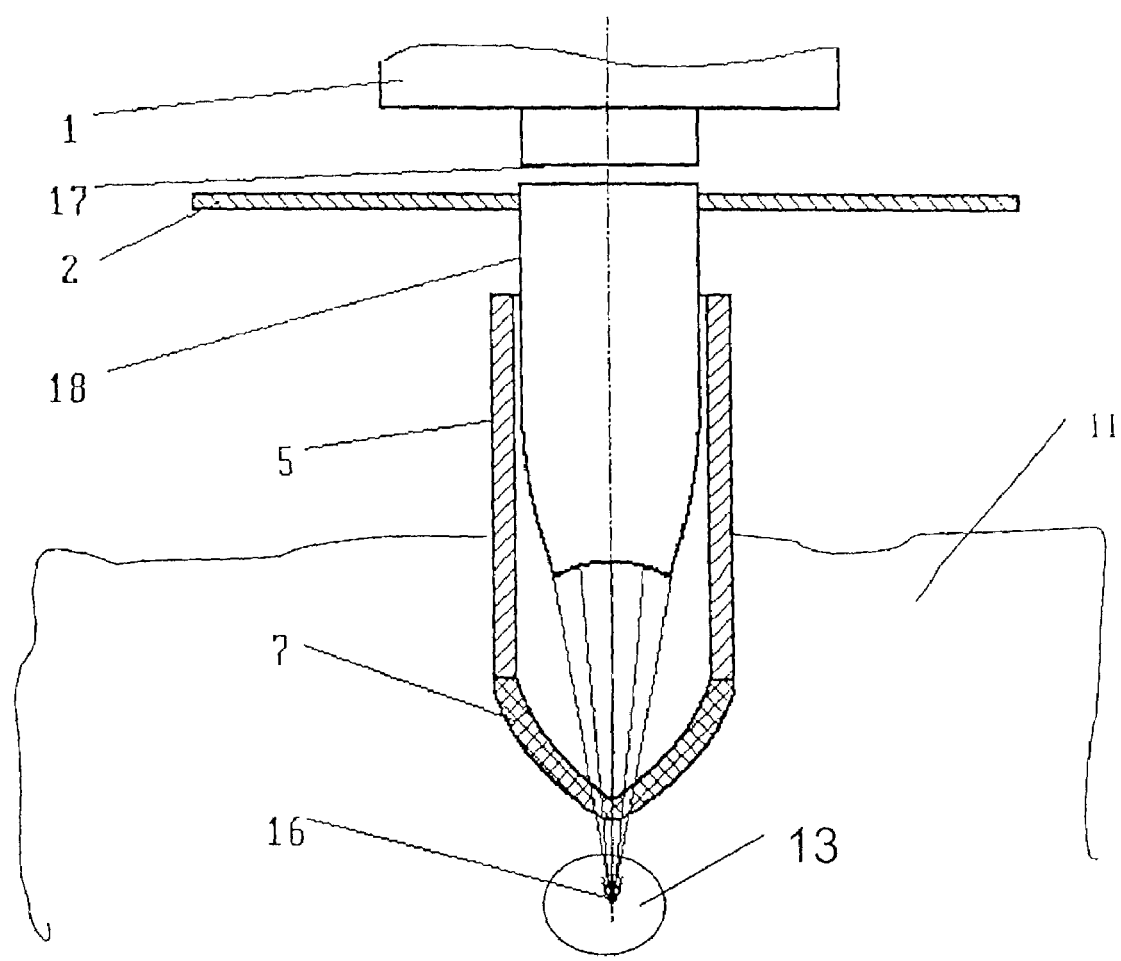
FIG. 5 - device with a lens effecting collimation and focusing of the source radiation.

In FIG. 5, lens 18 is forming a beam focused in the point 16 situated inside of the pathological locus 13, out of radiation of the source 1 having relatively large outlet aperture 17. The upper part of the lens 18 has parallel channels and plays a role of collimator. In this part of the lens, quasi-parallel beam of the particles forms, which id transmitted through its channels. After that, similar to ordinary lens for quasi-parallel radiation focusing, it is transformed into focused beam coming out of the lower end of the lens 18. Protective shield 2 protects patient 11 against radiation of the source 1, scattering past the lens 18.

In all the cases considered the radiation used, though created by a source located outside of the patient's body, doesn't affect healthy tissues situated on the way to the pathological locus. This is ensured due to the fact of healthy tissues being mechanically isolated from the radiation beam path by the probe walls, as well as to their shielding effect. For that, they are made radio-opaque to the radiation used. Although oriented radiation beam directed into the probe may not transverse walls of the probe, if being shaped sufficiently accurately, this measure is an additional guarantee of radiation being emitted only through portions of the distal end of the probe intended for this purpose.

Figure 6:
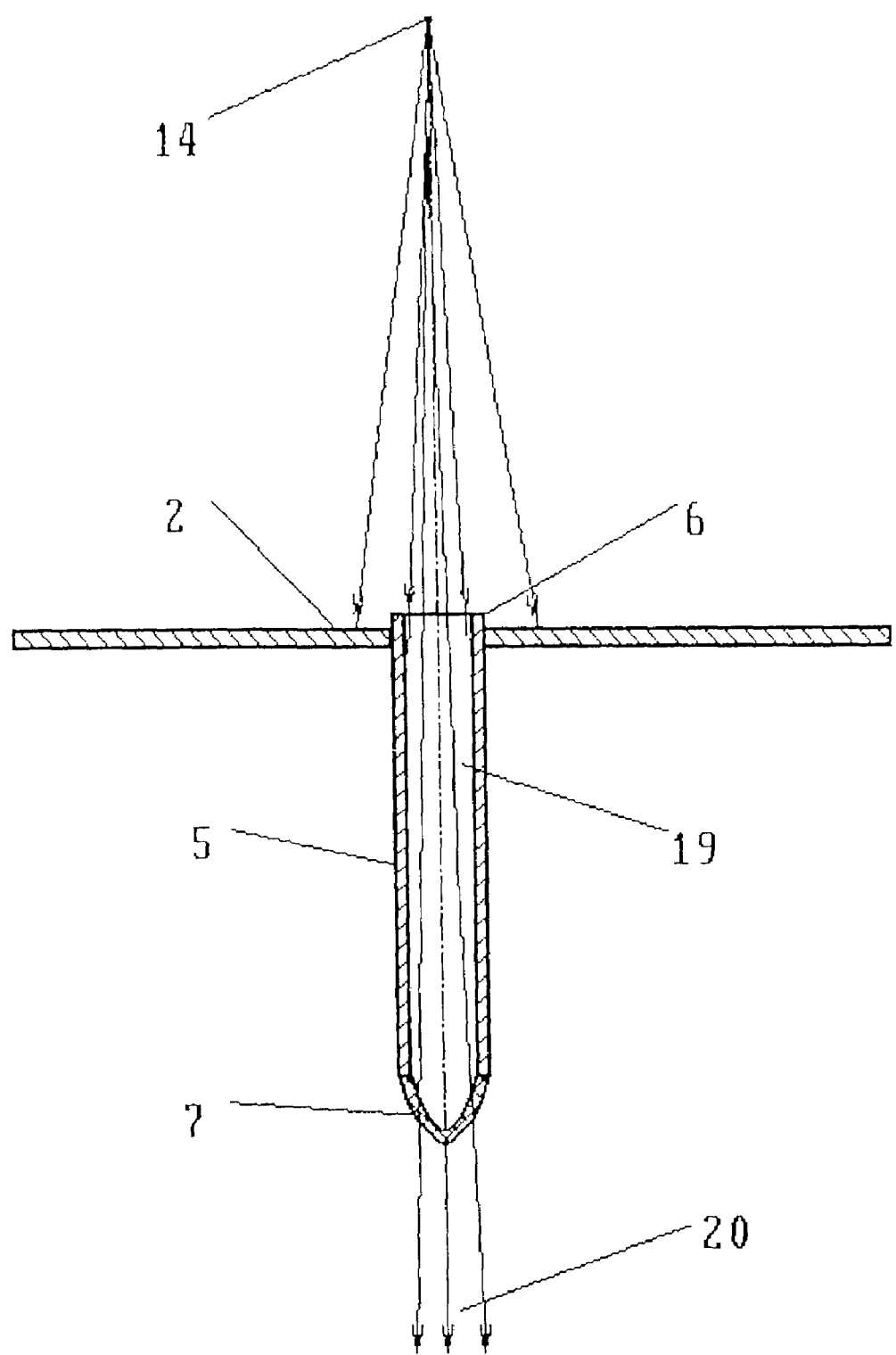
FIG. 6 - the probe serving simultaneously as a collimator with a single channel.

FIG. 6 demonstrates utilization of the device, in which shaping of the close-to-parallel beam going out of the distal end 7 of the probe 5 is effected by the probe itself. In the given case it functions as a collimator having single channel formed by side walls of the probe 5. With corresponding selection of the probe length and distance between its proximal end 6 and outlet aperture 14 of the radiation source, radiation 20 emerging from the distal end 7 has a small divergence angle and is close to parallel. Such work of the device is equivalent to placing of the means of quasi-parallel particle beam shaping inside of the probe.

In order to effect radiation treatment, it is possible to use simultaneously several probes introduced into different portions of a tumor.

In all the cases of utilization of X-ray source as a radiation source, the latter may be executed with a divided anode for on-line changes in the particles energy.

Figure 7:
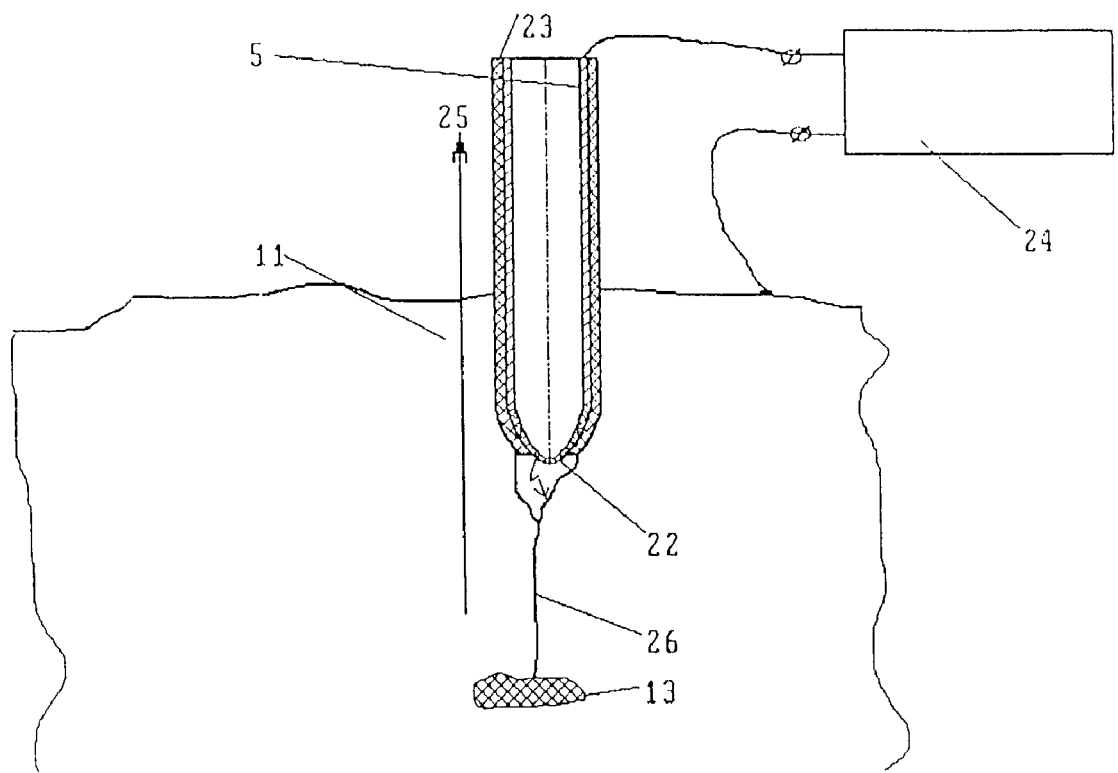
FIG. 7 - utilization of the device in combination with coagulator.

In order to ensure coagulation of wound channel arising in the course of puncture with a probe after completion of treatment procedure, the latter may be made electrically conductive and having on the outside (see FIG. 7) an insulating coating 23, except for the most remote portion 22 of the distal end. In this case, the probe should have possibility of being connected to electrocoagulator 24. On applying electric voltage from the coagulator between the probe 5 and body of patient 11 in the course of probe removal (arrow 25 in FIG. 7), "welding" of the wound channel 26 takes place. It prevents spreading of tumor 13 cells beyond the malignant locus (in this case, technique used is similar to that described in the patent of Russian Federation No. 2120787 [7]).

A secondary target may be located in the distal end of the probe. In this case, source radiation dissipated with a secondary target or secondary radiation of a target is used for radiation treatment.

Figure 8:
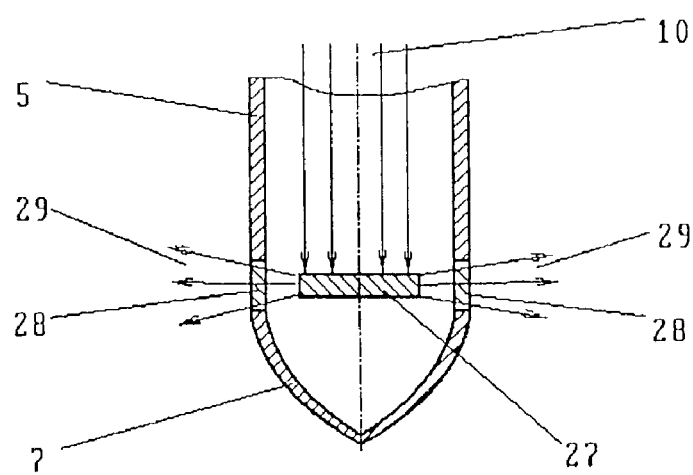
FIG. 8 - distal end of the probe with a secondary target installed in it, which is being irradiated with a quasi-parallel beam.

FIG. 8 demonstrates a case of utilization of radiation 29 excited in the secondary target material, which is brought out through windows 28 transparent for this kind of radiation. Those latters are situated in such a way as to form desired directional pattern of emergent radiation. For example, in case of uniform distribution of windows in a narrow strip over perimeter of the distal end 7, radiation will be concentrated in a narrow spherical sector. By changing depth of the probe introduction into the body of patient (in particular, into the tumor), position of this sector may be regulated for treatment of the selected part of the tumor. At that, different treatment tactics may be realized. For example, the probe may be displaced at variable speed or brought to stop for different time periods in different locations, thus regulating the degree of radiation exposure of different parts of the tumor, depending on its size in the direction perpendicular to longitudinal axis of the probe.

Figure 9:
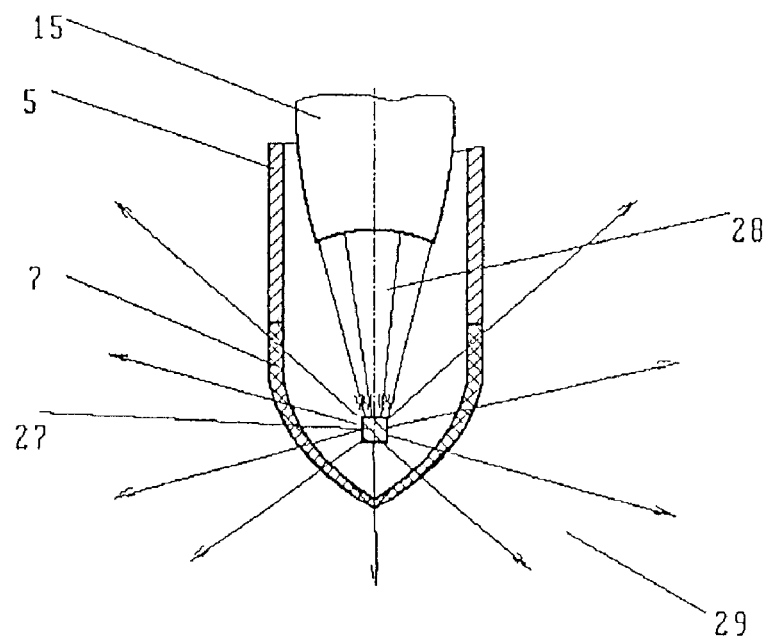
FIG. 9 - distal end of the probe with a secondary target installed in it, which is being irradiated with a focused beam.

FIG. 9 demonstrates utilization of radiation dissipated by the secondary target 27. Due to isotropic nature of the latter, by making the distal end 7 of the probe radiolucent and target locating close to the most remote part of the distal end, may be obtained nearly omnidirectional radiation 29, including spreading partially backwards (upward in FIG. 9). Introduction of the distal end 7 directly into the tumor ensures irradiation of the largest part of tumor tissues surrounding this end.

Figure 10:
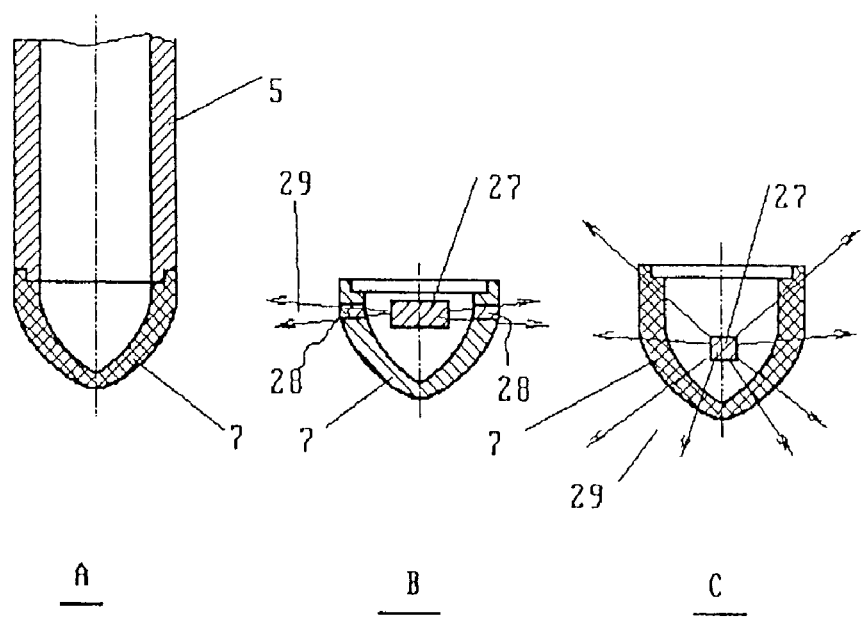
FIG. 10 - a probe with several removable distal ends.

By utilizing secondary targets, the advantages of the device proposed, which requires no evacuation of the probe, are realized to a still greater extent. The replacement is made possible not only of the probe as a whole, but also of its distal end 7, for changeover from one type of the secondary target used to the another one. FIG. 10 demonstrates realization of the probe 5 with a removable distal end 7 and embodiments of the distal end with two discussed above types of the secondary targets 27 and formation of two kinds of directional patterns of secondary radiation 28, 29 (see FIGS. 10, A, B, and C, correspondingly).

In order to change characteristics of dissipated and secondary radiation, distal end of the probe may be made split with a possibility of replacement of the target mounted in it. At that, secondary target mounted in the distal end of the probe is one of the several in the device set supplied, for example, made of different metals.

The probe 5 may have one of the several distal ends in the device set executed with different transparency ratios of surface portions of the distal end of the probe for radiation dissipated and excited in the secondary target material.

INDUSTRIAL APPLICABILITY

The device proposed may be realized by utilization both typical industrially manufactured radiation sources, such as X-ray tubes, and sources of neutron radiation and radioisotopes.

SOURCES OF INFORMATION

1. Aspects of Clinical Dosimetry, Ed. R. V. Stavitskij, Moscow, "MNPI", 2000 (in Russian).

2. Radiation Therapy of Malignant Tumors. Guide for Physicians. Ed. Prof. E. S. Kiseleva, Moscow, "Meditsina" Publishing House, 1996 (in Russian).

3. M. A. Kumakhov. X-ray means of location determination and radiation therapy of malignant neoplasms. International application PCT/RU 00/00273, international publication WO 01/29845A1, 26 Apr. 2001.

4. Nomikos et al. Miniaturized low power X-ray source. U.S. Pat. No. 5,153,900, publ. 06 Oct. 1992.

5. Advances in Neutron Capture Therapy. Editors: B. Larsson, J. Crawford, and R. Weinrech. Elsevier, 1997.

6. M. A. Kumakhov. A history of the X-Ray and neutron capillary optics. Optic of beams, p.p. 3-17, Moscow, 1993.

7. S. A. Astrakhantsev et al., Needle device for biopsy and coagulation. Patent of Russian Federation No.2120787, publ. 27 Oct. 1998.

The invention claimed is:

1. A device for performing radiation therapy comprising:
a sharpened hollow probe having dimensions of a puncture needle for biopsy and insertable into a patient's body, the hollow probe having a proximal end portion and a distal end portion for approaching or being introduced directly into a pathological locus, and
a beam shaping unit for shaping a beam of radiation particles generated by a source of x-rays, gamma radiation, or neutrons, the beam shaping unit is made in a form of a lens including multiple curved radiation transmission channels for forming a quasi-parallel or focused beam directed along a longitudinal axis of the hollow probe, wherein
the lens is at least partially arranged in the hollow probe, and
the proximal end portion of the hollow probe is non-transparent for the radiation particles.

2. The device of claim 1, wherein the hollow needle is removable from the device.

3. The device of claim 1, wherein a secondary target arranged in the hollow probe, adjacent to the distal end portion for scattering radiation incident at the secondary target or for exciting secondary radiation.

4. A device for performing radiation therapy comprising:
a hollow needle insertable into a patient's body, the hollow needle having a proximal end portion and a distal end portion for approaching or being introduced directly into a pathological locus;
a beam shaping unit for shaping a beam of radiation particles generated by a source of x-rays, gamma radiation, or neutrons, the beam shaping unit including a collimator or a lens for directing the beam along a longitudinal axis of the hollow needle, the beam shaping unit being at least partially arranged in the hollow needle, the proximal end portion of the hollow needle being non-transparent for the radiation particles; and
a secondary target arranged in the hollow needle, adjacent to the distal end portion for scattering radiation incident at the secondary target or for exciting secondary radiation.

5. The device according to claim 4, wherein the distal end portion is removable from the hollow needle.

6. The device according to claim 5, wherein the secondary target is replaceable.

7. A device for performing radiation therapy comprising:
a hollow needle for introduction into a patient's body, the hollow needle having a proximal end portion and a distal end portion for approaching or being introduced directly into a pathological locus,
a beam shaping unit for shaping a beam of radiation particles generated by a source of x-rays, gamma radiation, or neutrons, the beam shaping unit including a collimator or a lens for directing the beam along a longitudinal axis of the hollow needle, the beam shaping unit being at least partially arranged in the hollow needle, and
a secondary target arranged in the hollow needle, adjacent to the distal end portion for scattering radiation incident at the secondary target or for exciting secondary radiation, wherein
the proximal end portion of the hollow needle being non-transparent for the radiation particles.

8. The device according to claim 7, wherein the distal end portion is removable from the hollow needle.

9. The device according to claim 8, wherein the secondary target is replaceable.

10. The device of claim 7, wherein the hollow needle has dimensions of a puncture needle for biopsy.

11. The device of claim 7, wherein the hollow needle is removable from the device.

* * * * *